United States Patent [19]

Nanne et al.

[11] 4,371,628

[45] Feb. 1, 1983

[54] PROCESS FOR THE PREPARATION OF AROMATIC HYDROCARBONS USING CRYSTALLINE SILICATES AS CATALYST

[75] Inventors: Johannes M. Nanne; Martin F. M. Post, both of Amsterdam, Netherlands

[73] Assignee: Shell Oil Company, Houston, Tex.

[21] Appl. No.: 172,734

[22] Filed: Jul. 28, 1980

[30] Foreign Application Priority Data

Aug. 2, 1979 [NL] Netherlands ..................... 7905941

[51] Int. Cl.³ .............................................. C07C 1/04
[52] U.S. Cl. .................................. 518/713; 518/714; 518/717; 518/719; 585/469; 252/455 Z; 252/431 N; 423/328
[58] Field of Search ............... 585/469; 518/714, 719, 518/713, 717

[56] References Cited

U.S. PATENT DOCUMENTS

| | | | |
|---|---|---|---|
| 4,086,262 | 4/1978 | Chang et al. | 518/719 X |
| 4,159,995 | 7/1979 | Haag et al. | 518/719 X |
| 4,180,516 | 12/1979 | Chang et al. | 518/714 |
| 4,208,305 | 6/1980 | Kouwenhoven et al. | 423/328 X |

FOREIGN PATENT DOCUMENTS 2006819   5/1979   United Kingdom ............... 518/719

*Primary Examiner*—Bernard Helfin
*Attorney, Agent, or Firm*—John M. Duncan; Ronald R. Reper

[57] ABSTRACT

A process for the preparation of crystalline iron silicates with certain critical ratios of components in the starting mixture results in silicates having improved catalytic properties in conversion processes.

11 Claims, No Drawings

PROCESS FOR THE PREPARATION OF AROMATIC HYDROCARBONS USING CRYSTALLINE SILICATES AS CATALYST

BACKGROUND OF THE INVENTION

The invention relates to a process for the preparation of crystalline iron silicates with improved catalytic properties.

Mixtures of carbon monoxide and hydrogen can be converted into aromatic hydrocarbon mixtures using a mixture of two catalysts of which one has the capability of catalyzing the conversion of an $H_2/CO$ mixture into acyclic oxygen-containing hydrocarbons and the other is a crystalline iron or aluminum silicate which has the capability of catalyzing the conversion of acyclic oxygen-containing hydrocarbons into aromatic hydrocarbons. The said crystalline iron and aluminum silicates are characterized in having the following properties:
(a) thermally stable up to a temperature above 600° C.,
(b) an X-ray powder diffraction pattern showing, inter alia, the reflections given in Table A,

TABLE A

| Radiation: Cu—Kα<br>2 θ | Wavelength 0.15418 nm<br>relative intensity |
|---|---|
| 7.8–8.2 | S |
| 8.7–9.1 | M |
| 11.8–12.1 | W |
| 12.4–12.7 | W |
| 14.6–14.9 | W |
| 15.4–15.7 | W |
| 15.8–16.1 | W |
| 17.6–17.9 | W |
| 19.2–19.5 | W |
| 20.2–20.6 | W |
| 20.7–21.1 | W |
| 23.1–23.4 | VS |
| 23.8–24.1 | VS |
| 24.2–24.8 | S |
| 29.7–30.1 | M | wherein the letters used have the following meanings: VS=very strong; S=strong; M=moderate; W=weak; θ=angle according to Bragg.

(c) in the formula which gives the composition of the silicate, expressed in moles of the oxides, and in which, in addition to oxides of hydrogen, alkali metal and silicon, there is present an oxide of a trivalent metal A selected from Al and Fe, the $A_2O_3/SiO_2$ molar ratio (for the sake of brevity further designated m in this patent application) is less than 0.1.

The crystalline silicates which are used in the catalyst mixtures may be prepared starting from an aqueous mixture which contains the following compounds: one or more compounds of an alkali metal (M), one or more quaternary alkylammonium compounds ($R_4NX$), one or more silicon compounds and one or more iron or aluminum compounds. The preparation is effected by maintaining the mixture at elevated temperature until the crystalline silicate has been formed, separating it from the mother liquor and calcining it. In the aqueous mixture from which the silicates are prepared the various compounds should be present in the following ratio, expressed in moles of the oxides:
$M_2O:(R_4N)_2O = 0.05-5$
$(R_4N)_2O:SiO_2 = 0.05-1$
$SiO_2:A_2O_3 > 10$, and
$H_2O:SiO_2 = 5-50$.

In an investigation by the Applicant concerning the use of the above-mentioned catalyst mixtures, in which an iron silicate has been incorporated as the crystalline silicate, for the preparation of aromatic hydrocarbon mixtures starting from $H_2/CO$ mixtures with an $H_2/CO$ molar ratio lower than 1.0, the activity of these catalyst mixtures was often found to be unsatisfactory.

Further investigation by the Applicant concerning this subject showed that the activity of these catalyst mixtures is greatly determined by the $[M_2O+(R_4N)_2O]/SiO_2$ and $M_2O/(R_4N)_2O$ molar ratios used in the aqueous mixture from which the crystalline iron silicate component of the catalyst mixture is prepared. It has been found that catalyst mixtures with optimum activity for the conversion of $H_2/CO$ molar ratio below 1.0 into aromatic hydrocarbon mixtures can be obtained by using in the catalyst mixtures a crystalline iron silicate component which has been prepared from an aqueous mixture in which the $[M_2O+(R_4N)_2O]/SiO_2$ molar ratio is 0.24–0.40 and the $M_2O/(R_4N)_2O$ molar ratio 0.4–1.0. The preparation of crystalline iron silicates having the properties mentioned under (a)–(c) from an aqueous mixture in which the amounts of quaternary alkylammonium compounds, alkali metal compounds and silicon compounds have been so chosen that the above-mentioned requirements concerning the molar ratios are satisfied, is novel.

SUMMARY OF THE INVENTION

The present patent application therefore relates to a novel process for the preparation of crystalline iron silicates having the properties mentioned under (a)–(c), in which process an aqueous mixture that contains the following compounds: one or more compounds of an alkali metal (M), one or more quaternary alkyl ammonium compounds ($R_4NX$), one or more silicon compounds and one or more iron compounds, in which mixture the various compounds are present in the following ratios, expressed in moles of the oxides:
$M_2O:(R_4N)_2O = 0.4-1.0$,
$[M_2O+(R_4N)_2O]:SiO_2 = 0.24-0.40$,
$SiO_2:Fe_2O_3 > 10$, and
$H_2O:SiO_2 = 5-50$,
is maintained at elevated temperature until the crystalline silicate has been formed, and this silicate, is separated from the mother liquor and calcined.

DESCRIPTION OF PREFERRED EMBODIMENTS

Although the above-mentioned crystalline aluminum silicates are closely related to the crystalline iron silicates, as regards their preparation, structure and properties, the investigation by the Applicant has surprisingly shown that, whilst variation of the $M_2O/(R_4N)_2O$ and $[M_2O+(R_4N)_2O]/SiO_2$ molar ratios in the aqueous mixture from which the crystalline iron silicate component of the catalyst mixture is prepared, has a great influence on the activity of the catalyst mixture for the conversion of $H_2/CO$ molar ratio below 1.0 into aromatic hydrocarbon mixtures, variation of the said molar ratios in the aqueous mixture for which the crystalline aluminum silicate component of the catalyst mixture is prepared, has no influence on the activity of the catalyst mixture for the said conversion.

Although the crystalline silicates prepared according to the invention are designated iron silicates, they may contain, in addition to iron, a small amount of aluminum. The silicon compounds, which are from an economic point of view suitable for the preparation of crystalline silicates on a technical scale, contain as a rule a small amount of aluminum as contaminant. As a rule, this aluminum is found, at least partly, in the silicate prepared.

The silicates prepared according to the invention has been defined, inter alia, with reference to the X-ray powder diffraction pattern. This pattern should contain, inter alia, the reflections listed in Table A. The complete X-ray powder diffraction pattern of a typical example of a silicate prepared according to the invention is shown in Table B (Radiation: Cu-Kα, wavelength: 0.15418 nm).

TABLE B

| 2 θ | relative intensity (100.I/I$_o$) | description |
|---|---|---|
| 8.00 | 55 | SP |
| 8.90 | 36 | SP |
| 9.10 | 20 | SR |
| 11.95 | 7 | NL |
| 12.55 | 3 | NL |
| 13.25 | 4 | NL |
| 13.95 | 10 | NL |
| 14.75 | 9 | BD |
| 15.55 | 7 | BD |
| 15.95 | 9 | BD |
| 17.75 | 5 | BD |
| 19.35 | 6 | NL |
| 20.40 | 9 | NL |
| 20.90 | 10 | NL |
| 21.80 | 4 | NL |
| 22.25 | 8 | NL |
| 23.25 | 100$^{(x)}$ | SP |
| 23.95 | 45 | SP |
| 24.40 | 27 | SP |
| 25.90 | 11 | BD |
| 26.70 | 9 | BD |
| 27.50 | 4 | NL |
| 29.30 | 7 | NL |
| 29.90 | 11 | BD |
| 31.25 | 2 | NL |
| 32.75 | 4 | NL |
| 34.40 | 4 | NL |
| 36.05 | 5 | BD |
| 37.50 | 4 | BD |
| 45.30 | 9 | BD |

$^{(x)}$I$_o$ = intensity of the strongest separate reflection present in the pattern.

The letters used in Table B for describing the reflections have the following meanings: SP = sharp; SR = shoulder; NL = normal; BD = broad; θ = angle according to Bragg.

The crystalline iron silicates are prepared, according to the invention, from an aqueous mixture containing the following compounds: one or more compounds of an alkali metal (M), one or more quaternary alkylammonium compounds (R$_4$NX), one or more silicon compounds and one or more iron compounds. The preparation of the silicates may be carried out both at atmospheric pressure and at elevated pressure. If reaction temperatures are used which are above the boiling point of the mixture, it is preferred to work under autogenous pressure in an autoclave. The silicates are preferably prepared by maintaining the mixture for at least four hours at a temperature between 90° and 300° C. and in particular at a temperature between 125° and 175° C. After the silicates have been formed the crystals are separated from the mother liquor, for instance by filtering, decanting or centrifuging. The crystal mass is then washed with water and finally dried and calcined.

Examples of suitable compounds that may be used in the preparation of the silicates according to the invention are nitrates, carbonates, hydroxides and oxides of alkali metals; quaternary alkylammonium bromides and hydroxides; sodium silicate, silicasols, silicic acid, waterfree colloidal silicasols and amorphous solid silicas, such as precipitated silicasols; oxides, hydroxides, normal salts and complex salts of iron. In the preparation of the silicates according to the invention it is preferred to start from an aqueous mixture in which M is present in a sodium compound and R$_4$NX is a tetrapropylammonium compound. In the preparation of the silicates according to the invention it is further preferred to start from an aqueous mixture in which the silicon and iron compounds are present in a ratio below 650 and in particular below 400, expressed in moles of the oxides.

In the preparation of crystalline iron or aluminum silicates which have the properties mentioned under (a)–(c) from an aqueous mixture contains as one of the components a quaternary alkylammonium compound, it has so far been considered to be a drawback that for obtaining silicates of the desired structure a rather high concentration of the said compound should be present in the aqueous mixture. The said organic compound, which is rather expensive in comparison with the other reaction components in the aqueous mixture, is only an expedient in the synthesis, because the compound is incorporated into the silicate, but the silicate does not contain any longer any organic components after calcination. In the investigation by the Applicant concerning the preparation of crystalline iron and aluminum silicates of the present type, it has been found that only a small part of the amount of quaternary alkylammonium compound used in the aqueous mixture is incorporated in the silicate, whilst the rest is left, substantially unchanged, in the mother liquor. It has further been found that the mother liquor originating from a previous silicate preparation can be used without difficulty as the starting liquid for a subsequent silicate preparation by incorporating therein the desired amounts of the various reaction components, such that, as regards the quaternary alkylammonium compound, incorporation of an amount equal to that consumed in a previous silicate preparation will suffice. Re-using the mother liquor of a previous silicate preparation in view of the quaternary alkylammonium compound still present therein, makes the preparation of the silicates much cheaper. Obviously, this measure is not restricted to the preparation of crystalline iron silicates according to the invention, but it may generally be used in the preparation of crystalline iron or aluminum silicates characterized in having the properties mentioned under (a)–(c), from an aqueous mixture containing as one of the components a quaternary alkylammonium compound.

Silicates prepared according to the invention may, for instance, be used as adsorbent and extractant, as drying agent, as ion exchanger and as catalyst or catalyst carrier in various catalytic processes, in particular the catalytic preparation of aromatic hydrocarbons from acyclic organic compounds. If the aim is to use the silicates prepared according to the invention as catalyst or catalyst carrier, it is preferred to reduce the alkali metal content of these silicates previously to less than 0.1%w and in particular to less than 0.01%w. The reduction of the alkalimetal content of the silicates can very conveniently by carried out by contacting them once or several times with an aqueous solution containing ammonium ions. From the NH$_4$+ silicates thus obtained the H+ silicates can be prepared by calcination. When they are used as catalyst the crystalline iron silicates may, if desired, be combined with a binder material such as bentonite or kaolin.

As explained hereinbefore, an important application of the silicates prepared according to the invention is their use in catalyst mixture for the preparation of an aromatic hydrocarbon mixture from an $H_2/CO$ mixture with an $H_2/CO$ molar ratio below 1.0. Such $H_2/CO$ mixtures can very suitably be prepared by steam gasification of a carbon-containing material. Examples of such materials are brown coal, anthracite, coke, crude mineral oil and fractions thereof and oils produced from tar sand and bituminous shale. The steam gasification is preferably carried out at a temperature between 900° and 1500° C. and a pressure between 10 and 50 bar. The preparation of the aromatic hydrocarbon mixture from an $H_2/CO$ mixture with an $H_2/CO$ molar ratio below 1.0, using a catalyst mixture containing a crystalline iron silicate prepared according to the invention, is preferably carried out at a temperature of 200°–500° C. and in particular of 300°–450° C., a pressure of 1–150 bar and in particular of 5–100 bar and a space velocity of 50–5000 and in particular of 300–3000 Nl gas/l catalyst/h. The two catalysts present in the catalyst mixture used in the preparation of an aromatic hydrocarbon mixture from an $H_2/CO$ mixture with an $H_2/CO$ molar ratio below 1.0, will for the sake of brevity, further be designated catalyst X and catalyst Y. Catalyst X is the catalyst which is capable of catalyzing the conversion of an $H_2/CO$ mixture into acyclic oxygen-containing hydrocarbons and catalyst Y is the crystalline iron silicate prepared according to the invention. Catalysts that are preferably used as X-catalysts are those which are capable of converting an $H_2/CO$ mixture into substantially methanol and/or dimethyl ether. If the aim is to prepare a product consisting substantially of hydrocarbons boiling in the gasoline range, catalyst X can very suitably be a catalyst which contains zinc together with chromium. When using such a catalyst, it is preferred to choose one in which the atomic percentage of zinc, based on the sum of zinc and chromium, is at least 60% and in particular 60–80%. If the aim is to prepare, in addition to hydrocarbons boiling in the gasoline range, a fuel gas with a high calorific value, catalyst X can very suitably be a catalyst which contains zinc together with copper. The catalyst mixture may be a macromixture or a micromixture. In the first case the catalyst mixture consists completely of catalyst X, and the other kind completely of catalyst Y. In the second case the catalyst mixture consists of one kind of macroparticles, each macroparticle being built up of a great number of microparticles of each of the catalysts X and Y. Catalyst mixtures in the form of micromixtures may be prepared, for instance, by thoroughly mixing a fine powder of catalyst X with a fine powder of catalyst Y and shaping the mixture into larger particles, for instance by extruding or tabletting. It is preferred to use the catalyst mixtures in the form of micromixtures. It is further preferred to use mixtures containing per part by volume of catalyst Y, 1–5 parts by volume of catalyst X.

Crystalline iron silicates prepared according to the invention have also been found very suitable as catalyst in the preparation of aromatic hydrocarbons and hydrogen from a paraffin with four carbon atoms in the molecule (a $C_4$ paraffin) or from a hydrocarbon mixture consisting of more than 75%w paraffins with at most four carbon atoms in the molecule ($C_4^-$ paraffins) and of more than 50%w $C_4$ paraffins. A preferred starting material in this process is a hydrocarbon mixture consisting of more than 75%w $C_4$ paraffins. A very suitable feed is a hydrocarbon mixture substantially consisting of $C_3$ and $C_4$ paraffins obtained as by-product in the production of mineral oil. The process is preferably carried out at a temperature of 350°–700° C. and in particular of 400°–600° C. and a space velocity of from 0.1 to 20 $g.g^{-1}.h^{-1}$ and in particular of from 0.5 to 10 $g.g^{-1}.h^{-1}$. In order to reach a high activity, aromatics selectivity and hydrogen selectivity in the process, it is preferred to carry it out at a pressure below 5 bar, using a crystalline iron silicate prepared according to the invention containing zinc as the promotor and whose m is at most 0.01. Special preference is given to carrying out the process at a pressure of 1–3 bar, using a crystalline iron silicate prepared according to the invention which contains 0.05–20%w zinc and in particular 0.1–5%w zinc and whose m is more than 0.0017 and in particular more than 0.0022.

Crystalline iron silicates prepared according to the invention have further been found very suitable as catalyst in the preparation of aromatic hydrocarbons from a monoolefin with at most four carbon atoms in the molecule (a $C_4^-$ monoolefin) or from a hydrocarbon mixture consisting of more than 75%w $C_4^-$ monoolefins. A preferred starting material in the process is a $C_3$ or $C_4$ monoolefin or a hydrocarbon mixture substantially consisting of one or more of these monoolefins. A very suitable feed is a hydrocarbon mixture substantially consisting of $C_3$ and/or $C_4$ monoolefins obtained as by-product in the catalytic or thermal cracking of hydrocarbons, in particular in the thermal cracking of hydrocarbons for the preparation of ethylene. The process is preferably carried out at a temperature of 350°–550° C. and in particular of 375°–500° C., a pressure of from 3 to 20 bar and in particular of from 5 to 15 bar and a space velocity of 1–20 $g.g^{-1}.h$ and in particular of 2–10 $g.g^{-1}.h^{-1}$. If desired, the process may be carried out in the presence of hydrogen. In order to reach in the process a high aromatics selectivity and a slight change of this selectivity with time, preference is given to carrying out the process using a crystalline iron silicate prepared according to the invention whose m is at least 0.005 and at most 0.01.

Crystalline iron silicates prepared according to the invention are further suitable as catalyst for upgrading gasoline fractions such as gasoline fractions, obtained by straight-run distillation of crude mineral oil, isomerates, reformates and gasoline fractions obtained by catalytic, thermal or hydrocracking. A considerable increase in octane number is effected by contacting the said gasoline fractions at elevated temperature with the crystalline iron silicates. Crystalline iron silicates prepared according to the invention have been found preeminently suitable as catalyst for upgrading reformates. The conversion of the reformate over the crystalline iron silicate is preferably carried out at a temperature of 250°–550° C. and in particular of 250°–450° C., a pressure of 5–225 bar and in particular of 10–150 bar and a space velocity of 0.1–250 $1.1^{-1}.h^{-1}$. The conversion is preferably carried out in the presence of hydrogen. Further, it is preferred to use as the catalyst a crystalline iron silicate containing one or more metals with hydrogenating activity, such as nickel or palladium. Crystalline iron silicates prepared according to the invention are also suitable as catalyst for the conversion of methanol into aromatic gasoline. A drawback of the last mentioned conversion is that special steps have to be taken to carry off the large amount of heat that is liberated. It has been found that this drawback can be avoided by using as the feed a mixture of methanol and one of the above-mentioned gasoline fractions as diluent. By contacting such a mixture at elevated temperature with a crystalline iron silicate prepared according to the invention as the catalyst, not only methanol is converted into aromatic gasoline, without the strongly exothermic character of this reaction being a problem, but also the quality of the gasoline fraction used as diluent is improved. The above-described catalytic conversion of a mixture of methanol and a gasoline fraction is by no means restricted to the use of a crystalline iron silicate prepared according to the invention as the catalyst. In general, crystalline iron or aluminum silicates having the properties mentioned under (a)–(c) are suitable catalysts for this purpose.

The invention will now be explained with reference to the following example:

EXAMPLE

Six crystalline silicates (silicates 1–6) were prepared by heating mixtures of $SiO_2$, $NaOH$, $[(C_3H_7)_4N]OH$ and either $NaAlO_2$, or $Fe(NO_3)_3$ for 24 hours in water in an autoclave at 150° C. under autogenous pressure. After the reaction mixtures had cooled down, the silicates formed were filtered off, washed with water until the pH of the wash water was about 8, dried at 120° C. and calcined at 500° C.

Silicates 1–6 had the following properties:
(a) thermally stable up to a temperature above 800° C.,
(b) an X-ray powder diffraction pattern, substantially equal to the one given in Table B,
(c) a value for m as given in Table C

TABLE C

| Silicate No. | $Al_2O_3/SiO_2$ | $Fe_2O_3/SiO_2$ |
|---|---|---|
| 1 | 0.0035 | — |
| 2 | 0.0034 | — |
| 3 | — | 0.0034 |
| 4 | — | 0.0034 |
| 5 | — | 0.0066 |
| 6 | — | 0.011 |

The molar composition of the aqueous mixtures from which silicates 1–6 were prepared can be represented as follows: x $Na_2O.4.5[(C_3H_7)_4N]_2O.y$ $Al_2O_3.z$ $Fe_2O_3.25$ $SiO_2.450$ $H_2O$ wherein x, y and z have the values given in Table D.

TABLE D

| Silicate No. | x | y | z | $Na_2O/[(C_3H_7)_4N]_2O$ molar ratio | $Na_2O + [(C_3H_7)_4N]_2O/SiO_2$ molar ratio |
|---|---|---|---|---|---|
| 1 | 3 | 0.039 | — | 0.67 | 0.38 |
| 2 | 1 | 0.063 | — | 0.22 | 0.22 |
| 3 | 3 | — | 0.040 | 0.67 | 0.38 |
| 4 | 1 | — | 0.063 | 0.22 | 0.22 |
| 5 | 3 | — | 0.063 | 0.67 | 0.38 |
| 6 | 3 | — | 0.125 | 0.67 | 0.38 |

Silicates 7–12 were prepared from silicates 1–6, respectively, by boiling silicates 1–6 with 1.0 molar $NH_4NO_3$ solution, washing with water, boiling again with 1.0 molar $NH_4NO_3$ solution and washing, drying at 120° C. and calcining at 500° C. Subsequently, four catalyst mixtures (catalyst mixtures A-D) were prepared by mixing a $ZnO-Cr_2O_3$ composition with each of the silicates 7–10. The atomic Zn percentage of the $ZnO-Cr_2O_3$ composition was 70%, based on the sum of Zn and Cr. The catalyst mixtures all contained per part by weight silicate 10 parts by weight of the $ZnO-Cr_2O_3$ composition. Finally, a catalyst E containing 0.88%w zinc was prepared by impregnating silicate 11 with an aqueous solution of $Zn(NO_3)_2$, followed by drying and calcining of the composition.

Catalyst mixtures A-D were tested for the preparation of an aromatic hydrocarbon mixture from an $H_2/CO$ mixture. The test was carried out in a 50-ml reactor containing a fixed catalyst bed having a volume of 7.5 ml. In four experiments an $H_2/CO$ mixture with an $H_2/CO$ molar ratio of 0.5 was conducted over each of the catalyst mixtures A-D at a temperature of 375° C., a pressure of 60 bar and a space velocity of 1000 $Nl.^{-1}.h^{-1}$. In all cases a product was obtained of which the $C_5^+$ fraction comprised more than 50%w aromatics. The other results of the experiments are listed in Table E.

TABLE E

| Exp. No. | Cat. mixture No. | Silicate No. | Conversion of the synthesis gas after 10 h, % |
|---|---|---|---|
| 1 | A | 7 | 50 |
| 2 | B | 8 | 50 |
| 3 | C | 9 | 49 |
| 4 | D | 10 | 43 |

Catalyst E was tested for the preparation of aromatic hydrocarbons and hydrogen from isobutane. The test was carrid out in a 50-ml reactor containing a fixed catalyst bed of 5 ml catalyst E. Isobutane was conducted over catalyst E at a temperature of 500° C., a pressure of 1.5 bar and a space velocity of 2 g isobutane/g catalyst/hour. The results of this experiment (experiment 5) are listed in Table F. The table includes:

(a) the activity =

$$\frac{\text{parts by weight (total product} - C_4 \text{ hydrocarbons in product)}}{\text{parts by weight total product}} \times 100$$

(b) the aromatics selectivity =

$$\frac{\text{parts by weight aromatic hydrocarbons in product}}{\text{parts by weight (total product} - C_4 \text{ hydrocarbons in product)}} \times 100$$

(c) the hydrogen selectivity =

$$\frac{\text{parts by weight hydrogen in product}}{\text{parts by weight (total product} - C_4 \text{ hydrocarbons in product}} \times 100$$

Silicate 11 was tested as the catalyst for preparing an aromatic hydrocarbon mixture from isobutene. The test was carried out in a 50-ml reactor containing a fixed catalyst bed of 5 ml silicate 11. Isobutene was conducted over the catalyst at 400° C., a pressure of 10 bar, a space velocity of 3.4 g isobutene/g silicate/h and an $H_2$/isobutene molar ratio 5:1. The results of this experiment (experiment 6) are listed in Table F. The table includes the aromatics selectivities (expressed as yield of aromatics in % based in isobutene feed) after 1 day and after 10 days.

Silicate 12 was tested as the catalyst for upgrading a $C_5^+$ gasoline fraction which had been obtained by catalytic reforming. The upgrading was carried out by contacting the $C_5^+$ reformate with silicate 12 at a temperature of 320° C., a pressure of 28 bar, a space velocity of 5 1.1$^{-1}$.h$^{-1}$ and an H$_2$/oil molar ratio of 2:1. The results of this experiment (experiment 7) are listed in Table F. The table includes the octane number and the composition of the C$_5$+ reformate and the C$_5$+ product.

TABLE F

| Experiment 5 | | |
|---|---|---|
| activity, % | | 54.5 |
| aromatics selectivity, % | | 50.4 |
| hydrogen selectivity, % | | 2.99 |
| Experiment 6 | | |
| aromatics selectivity after 1 day, % | | 23 |
| aromatics selectivity after 10 days, % | | 19 |
| Experiment 7 | C$_5$+ reformate | C$_5$+ product |
| Octane number (RON-O) | 88.9 | 95.3 |
| aromatics content, % w | 54.5 | 66.0 |
| naphthenes content, % w | 3.5 | 3.6 |
| paraffins content, % w | 42.0 | 30.4 |

Of the silicates listed in Table D, only the silicates 3, 5 and 6 were prepared according to the invention. The silicates 1, 2 and 4 are outside the scope of the invention. They have been included in the patent application for comparison. Of the experiments listed in the Tables E and F, only the experiments 3 and 5–7 were carried out using a catalyst which contained a crystalline iron silicate prepared according to the invention. The experiments 1, 2 and 4 are outside the scope of the invention. They have been included in the patent application for comparison.

The results listed in Table E show that in the conversion of an H$_2$/CO mixture with an H$_2$/CO molar ratio below 1.0 into an aromatic hydrocarbon mixture, using a catalyst mixture containing a crystalline aluminum silicate, the activity of the catalyst mixture is independent of the Na$_2$O/[(CH$_3$)$_4$N]$_2$O and Na$_2$O+[(CH$_3$)$_4$N]$_2$O/SiO$_2$ molar ratios in the base mixture from which the silicate concerned was prepared. The results further show that, when using a catalyst mixture containing a crystalline iron silicate, the activity of the catalyst mixture for the said conversion is greatly dependent on the said molar ratios in the base mixture and that by a proper choice of these molar ratios catalyst mixtures can be prepared with a high activity for the said conversion.

The results of the experiments 5–7 show that crystalline iron silicates prepared according to the invention are also very suitable as catalyst in:
(a) the preparation of aromatic hydrocarbons and hydrogen from lower paraffins,
(b) the preparation of an aromatic hydrocarbon mixture from lower olefins, and
(c) the upgrading of gasolines prepared by catalytic reforming.

What is claimed is:

1. A process for the preparation of an aromatic hydrocarbon mixture which comprises contacting at an elevated temperature and reaction conditions an H$_2$/CO mixture having an H$_2$/CO molar ratio below 1.0, with a mixture of two catalysts of which one has the capability of catalyzing the conversion of an H$_2$/CO mixture into acyclic oxygen-containing hydrocarbons and the other is a crystalline iron silicate having the following properties:

(a) thermally stable up to a temperature above 600° C.,
(b) an X-ray powder diffraction pattern having, inter alia, the reflections given in Table A of the specification,
(c) the composition of the silicate, expressed in moles of the oxides, includes oxides of hydrogen, alkali metal and silicon, and iron and has an Fe$_2$O$_3$/SiO$_2$ molar ratio (m) less than 0.1, said crystalline iron silicate having been prepared by a process comprising maintaining at an elevated temperature an aqueous mixture containing: at least one compound of an alkali metal (M), at least one quaternary alkylammonium compound (R$_4$NX), at least one silicon compound and at least one iron compound, in which mixture the compounds are present in the following ratios, expressed in moles of the oxides:
M$_2$O: (R$_4$N)$_2$O = 0.4–1.0,
[M$_2$O+(R$_4$N)$_2$O]:SiO$_2$ = 0.24–0.40,
SiO$_2$:Fe$_2$O$_3$ > 10, and
H$_2$O:SiO$_2$ = 5–50,
until the crystalline silicate has formed, and separating the silicate from the mother liquor; and separating an aromatic hydrocarbon mixture from the reaction product.

2. A process according to claim 1, wherein the catalyst mixture is built up of a catalyst X and a catalyst Y, catalyst X being capable of converting an H$_2$/CO mixture into substantially methanol and/or dimethyl ether and catalyst Y being the crystalline iron silicate.

3. A process according to claim 2, wherein the X-catalyst composition contains zinc together with chromium.

4. A process according to claim 2, where X-catalyst composition contains zinc together with copper.

5. A process according to claim 1, wherein the reaction conditions comprise a temperature of 200°–500° C., a pressure of 1–150 bar and a space velocity of 50–5000 Nl gas/l catalyst/h.

6. A process according to claim 5, wherein the temperature is 300°–450° C., the pressure is 5–100 bar and the space velocity is 300–3000 Nl gas/l catalyst/h.

7. A process according to claim 1, wherein the compound R$_4$NX is a tetrapropylammonium compound and the alkali metal compound is a sodium compound.

8. A process according to claim 1, wherein the mixture is maintained at a temperature between about 90° and 300° C. for at least four hours.

9. A process according to claim 8, wherein the temperature is between 125° and 175° C.

10. A process according to claim 1, wherein in the starting aqueous mixture the ratio of the silicon to iron compounds, expressed in moles of the oxides is below 650.

11. A process according to claim 10, wherein the ratio of the silicon to iron compounds, expressed in moles of the oxides, is below 400.

* * * * *